United States Patent [19]

Horzewski et al.

[11] Patent Number: 4,771,777
[45] Date of Patent: Sep. 20, 1988

[54] PERFUSION TYPE BALLOON DILATATION CATHETER, APPARATUS AND METHOD

[75] Inventors: Michael J. Horzewski, Sunnyvale; Richard L. Mueller, Jr., Mountain View, both of Calif.

[73] Assignee: Advanced Cardiovascular Systems, Inc., Mountain View, Calif.

[21] Appl. No.: 649

[22] Filed: Jan. 6, 1987

[51] Int. Cl.[4] .................................. A61M 29/02
[52] U.S. Cl. ..................... 128/344; 604/101; 604/102
[58] Field of Search ............ 604/96, 101, 102; 128/344

[56] References Cited

U.S. PATENT DOCUMENTS

| | | | |
|---|---|---|---|
| 3,769,981 | 11/1973 | McWhorter | 604/96 |
| 3,788,326 | 1/1974 | Jacobs | 604/161 |
| 4,299,226 | 11/1981 | Banka | 128/344 |
| 4,423,725 | 1/1984 | Baran et al. | 604/101 |
| 4,445,892 | 5/1984 | Hussein et al. | 604/101 |
| 4,453,545 | 6/1984 | Inoue | 604/101 |
| 4,610,662 | 9/1986 | Weikl et al. | 604/101 |
| 4,616,653 | 10/1986 | Samson et al. | 604/170 |
| 4,652,258 | 3/1987 | Drach | 604/96 |
| 4,655,746 | 4/1987 | Daniels et al. | 604/101 |

*Primary Examiner*—C. Fred Rosenbaum
*Assistant Examiner*—Gene B. Kartchner
*Attorney, Agent, or Firm*—Fulwider, Patton, Rieber, Lee & Utecht

[57] ABSTRACT

Perfusion-type balloon dilatation apparatus having a guiding catheter with proximal and distal extremities and with a flow passage extending therethrough. A balloon dilatation catheter is disposed in the guiding catheter. The balloon dilatation catheter is comprised of a flexible elongate tubular member having proximal and distal extremities and having a first lumen extending therethrough. First and second inflatable balloons are carried by the tubular member and having their interiors in communication with the first lumen in the tubular member. The first balloon is positioned within the guiding catheter. The second balloon is positioned adjacent the distal extremity of the tubular member. A second lumen is carried by the tubular member and extends through the first and second balloons and through the distal extremity of the tubular member. The second lumen has an opening proximal of the first balloon and opens into the interior of the guiding catheter. An adapter is carried by the proximal extremity of the guiding catheter and provides a liquid-tight seal between the guiding catheter and the dilatation catheter and also provides an inlet through which liquid can be introduced so that it can travel through the flow passage in the guiding catheter and into the second lumen carried by the dilatation catheter so that the liquid can flow through the second lumen beyond the second inflatable balloon.

13 Claims, 2 Drawing Sheets

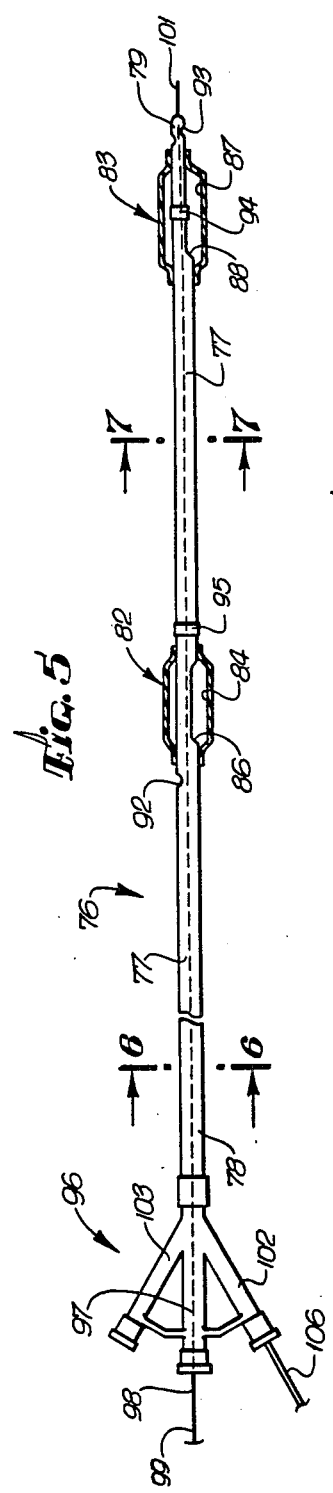
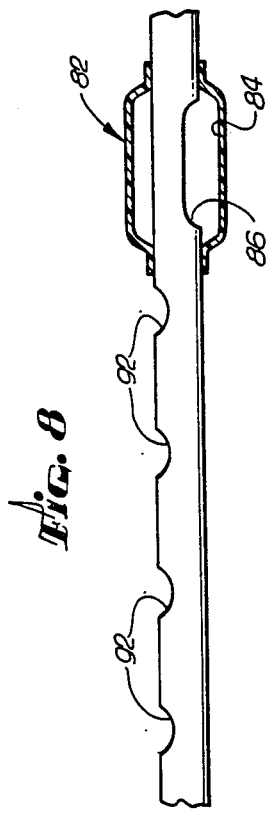
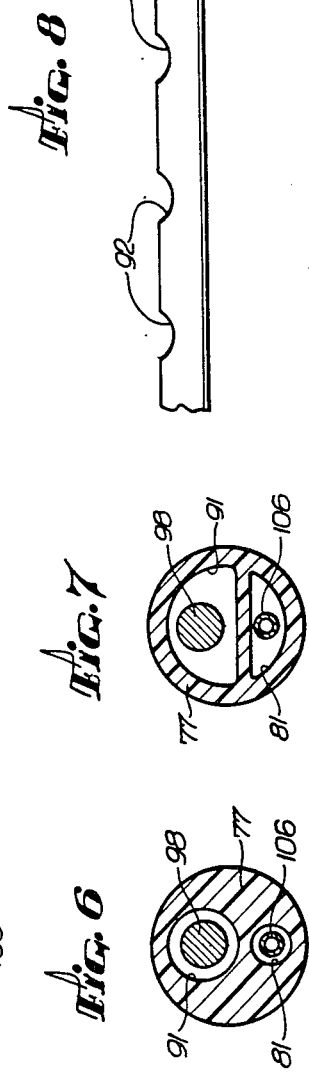
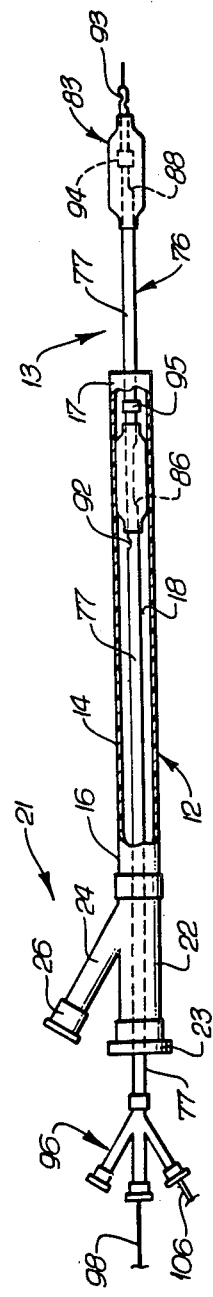

PERFUSION TYPE BALLOON DILATATION CATHETER, APPARATUS AND METHOD

This invention relates to a perfusion-type balloon dilatation apparatus and method and more particularly, to one which has the capabilities to pump blood to the distal side of a stenosis.

In angioplasty procedures, it has been found that there has been a restenosis rate ranging from 15 to 30%. There is a belief that this restenosis rate can be lowered if longer inflation times are utilized for inflating the balloon while in a stenosis so that the stenosis will remain open and not restenose. In order to accomplish such longer inflation times, there is a need to provide blood flow to the portions of the heart distal of the stenosis during the time that longer inflation times are taking place. There is a need for a catheter, aparatus and method which will make this possible.

In general, it is an object of the present invention to provide a balloon dilatation catheter, apparatus and method which will make it possible to accomplish blood perfusion in a region which is distal of the stenosis in which the inflated balloon is positioned.

Another object of the invention is to provide a catheter, apparatus and method of the above character which makes it possible to achieve substantially normal coronary flow during a dilatation procedure.

Another object of the invention is to provide a catheter, apparatus and method of the above character which makes it possible to achieve such flows at relatively low pressures with minimal turbulence and hemolysis.

Additional objects and features of the invention will appear in conjunction with the following description which is set forth in detail with the accompanying drawings.

FIG. 5 is a side elevational view of another embodiment of a balloon dilatation catheter incorporating the present invention.

FIG. 6 is a cross sectional view taken along the line 6—6 of FIG. 5.

FIG. 7 is a cross sectional view taken along the line 7—7 of FIG. 5.

FIG. 8 is a partial side elevational view of another embodiment of the catheter shown in FIG. 5.

FIG. 9 is a side elevational view partially in cross section of a balloon dilatation apparatus utilizing the balloon dilatation catheter shown in FIG. 5.

Figure 1:
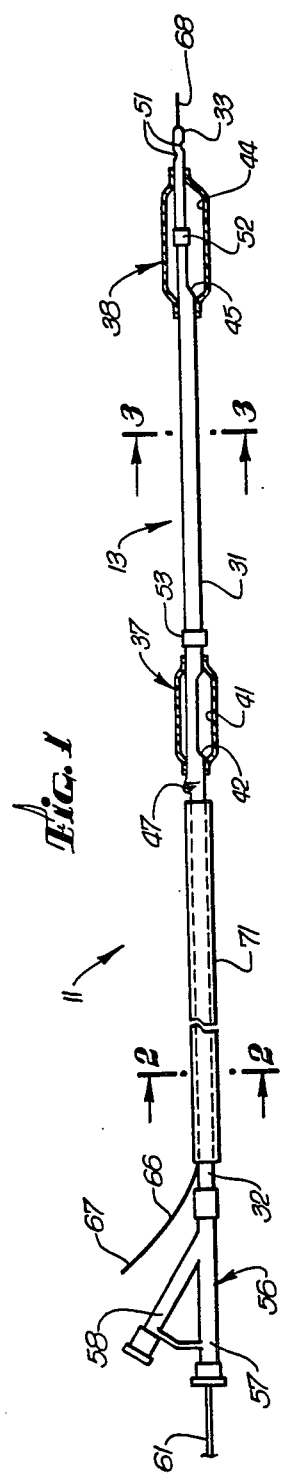
FIG. 1 is a side elevational view of a perfursion type balloon dilatation catheter incorporating the present invention.

In general the perfusion-type balloon dilatation catheter and apparatus consists of a guide catheter and a balloon dilatation catheter. The guiding catheter has proximal and distal extremities and has a flow passage extending therethrough. The balloon dilatation catheter is disposed in the flow passage in the guiding catheter and is comprised of a flexible elongate tubular element having proximal and distal extremities and having a first lumen extending therethrough. First and second inflatable balloons are carried by the tubular member and have their interiors in communication with a lumen in the tubular member. The first balloon is positioned within and near the proximal extremity of the guiding catheter. The second balloon is positioned adjacent the distal extremity of the tubular member. A second lumen is carried by the tubular member and extends through the second balloon and through the distal extremity of the tubular member. The second lumen has an inlet opening proximal of the first balloon which opens into the interior of the guiding catheter. An adapter is carried by the proximal extremity of the guiding catheter and has a liquid-tight seal formed about the balloon dilatation catheter and is provided with an inlet port through which blood can be introduced into the flow passage in the guiding catheter and then into the inlet of the second lumen so that blood can flow through the second lumen out the distal extremity of the tubular member.

More in particular, the perfusion-type balloon dilatation apparatus 11 and the method of the present invention consists of a guiding catheter 12 and a balloon dilatation catheter 13. The guiding catheter 12 as shown in FIG. 9 is of a conventional construction and is provided with an elongate flexible tubular member 14 formed of a suitable material such as plastic and has proximal and distal extremities 16 and 17. The distal extremity 17 can be provided with any desired conventional bend.

The tubular member 14 is provided with a flow passage or lumen 18 which extends therethrough from the proximal to the distal extremities. By way of example, the tubular member 14 can have an outside diameter of 0.078 to 0.116 inch and an inside diameter of 0.040 to 0.078 inch.

The guiding catheter 12 is also provided with an adapter 21 which also is of a conventional type. It is provided with a hemostatic valve 22 through which the balloon dilatation catheter 13 can be introduced and a liquid-tight seal formed therein with respect to the same by tightening a knob 23. The adapter 21 is also provided with a side arm 24 which is provided with a Luer-type fitting 26 at its extremity which can be secured to another Luer fitting connected to another tubular member and/or a pump through which blood can be supplied as hereinafter described.

The balloon dilatation catheter 13 of the present invention consists of a flexible elongate tubular member 31 formed of a suitable polyolefin or polyolefin alloy to provided a shaft for the balloon dilatation catheter of varying stiffness with the stiffness being greatest at the proximal extremity 32 of the tubular member with decreasing stiffness in a direction toward the distal extremity 33 to provide maximum force or pushability in transmission in the straight sections of the tubular member 31 and lesser stiffness for increased flexibility and trackability in the distal portion to negotiate the aortic arch and lead into the coronary vasculature. For maximum flexibility and trackability the extreme distal extremity can be made of very soft polyolefin. As explained in co-pending application Ser. No. 000,653, filed Jan. 6, 1987 different degrees of stiffness in the shaft can be readily obtained by forming portions of the tubular member from different compositions of a suitable polyolefin. For example, the proximal portion can be formed of a high density polyolefin compound, whereas the more flexible portions can be formed of a mixture of high density polyolefin and low density polyolefin with the tip being formed of a very low density polyolefin. The various portions can be heat bonded together as explained in co-pending application Ser. No. 000,653, filed Jan. 6, 1987.

A first lumen 36 is provided in the tubular member 31 which extends from the proximal extremity of the tubular member 31 into a region at least near the distal extremity of the tubular member 31. As hereinafter described, the first lumen 36 can be identified as a ballon inflation/deflation lumen. First and second inflatable balloons 37 and 38 are carried by the tubular member 31. The first and second balloons 37 and 38 are formed in a suitable manner, as for example, of soft polyolefin. The material for the balloons can be irradiated if desired so that the proximal and distal extremities of the balloon can be secured to the tubular member 31 by suitable means such as heat shrinking the same onto the tubular member or, alternatively, by utilizing an adhesive.

The second balloon 38 is positioned near the distal extremity of the tubular member 31 and serves as a conventional dilatation balloon for performing dilatation operations on a stenosis as hereinafter described. The first balloon 37 is provided for an entirely different purpose and is proximal of the distal or second balloon 38 and normally is positioned a suitable distance as, for example, approximately 20 centimeters from the distal or second balloon 38. The balloon 37 is disposed within and adjacent the proximal extremity of the guiding catheter 12 when the balloon dilatation catheter 13 is positioned in the guiding catheter and is being used to perform an enlargement of a stenosis.

As hereinafter described, the first balloon 37 is provided for forming a liquid-tight seal between the balloon dilatation catheter 13 and the inner wall of the guiding catheter 12. The distal or second balloon can have a suitable diameter as, for example, ranging from 1.5 to 4.0 centimeters. The proximal or first balloon 37 can have a diameter which is sufficient to close off the flow passage 18 in the guiding catheter 12. Thus if the guiding catheter has an inside diameter of 0.040 to 0.078 inch, the proximal or first balloon 37 should have a corresponding diameter but slightly larger.

Means is provided for establishing communication between the interior 41 of the first balloon 37 and the lumen 36 extending through the tubular member 31. As shown this is accomplished by providing at least one elongate slot 42 in the tubular member 31 which is in communication with the interior 41 of the first balloon 37. The interior 44 of the second balloon 38 is in communication with the distal extremity of the first lumen 36 through an elongate slot 45. Although only a single lumen, namely the first lumen 36, has been provided for inflating and deflating both of the balloons 37 and 38, it should be appreciated that if desired, a separate balloon inflation lumen can be provided for each of the balloons. However, this is normally undesirable because this would require the formation of an additional lumen and possibly make it necessary to increase the diameter of the tubular member 31.

Figure 4:
FIG. 4 is an enlarged cross sectional view of a portion of the catheter shown in FIG. 1.
Figure 4:
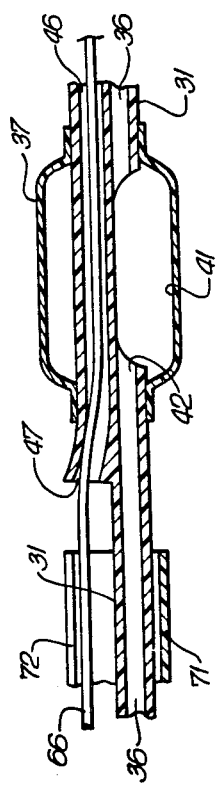

A second lumen 46 is carried by the tubular member 31. The second lumen 46 can be formed into a separate sleeve carried by the tubular member 31 or alternatively, as shown, it can be formed in the tubular member 31 itself. Thus, the second lumen 46 as shown in FIG. 4 has an inlet opening 47 which is just proximal of the first balloon 37 and extends through the portion of the tubular member 31 extending between the first and second balloons 37 and 38 through the second balloon 38 and through the distal extremity of the tubular member 31.

Figure 3:
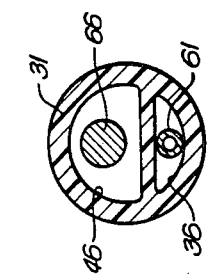
FIG. 3 is a cross sectional view taken along the line 3—3 of FIG. 1.
Figure 2:
FIG. 2 is a cross sectional view taken along the line 2—2 of FIG. 1.
Figure 2:
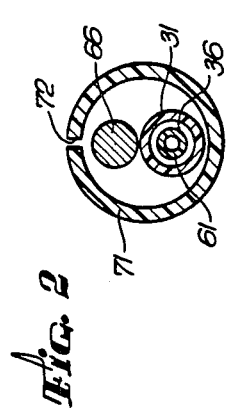

As shown in FIG. 2, the first or balloon inflation/deflation lumen 36 can have a suitable diameter such as an inside diameter of approximately 0.012 inches for the tubular member 31 and an outside diameter of 0.020 inches. As shown in FIG. 3, this first lumen 36 in that region can have an arcuate shape having suitable dimensions such as approximately 0.024×0.011 inches. The second lumen 46 can have a diameter of approximately 0.041×0.029 inches and as hereinafter explained serves as a guide wire/flow lumen. The outside diameter of the tubular member 31 in the region of FIG. 3 has an outside diameter of approximately 0.060 inch.

The distal extremity of the tubular member 31 is provided with a plurality of radially and longitudinally spaced openings 51 which are distal of the second balloon 38 and which are in communication with the second lumen 46. A radiopaque marker of a suitable material such as gold or platinum band or coil 52 is placed on the tubular member 31 equidistant between the ends of the distal balloon 38. A similar radiopaque marker 53 is provided on the member 31 just distal of the balloon 37 to indicate the position of the balloon 37.

An adapter 56 of a conventional type is secured to the proximal extremity of the tubular member 31 and is provided with a central arm 57 which is in communication with the first lumen 36. The adapter 56 is provided with a side arm 58 which is also in communication with the first lumen 36 and which can be utilized for introducing a liquid as, for example, a radiopaque contrast liquid for inflating and deflating the balloons 37 and 38.

Suitable means is provided for venting the second or distal balloon 38 and as shown can consist of a vent tube 61 of a conventional type such as a flexible stainless steel tubular member which is inserted through the central arm 57 through the first lumen 36 until it extends into the balloon 38 near the distal extremity of the second or distal balloon 38. Thus it can be seen that when a liquid is introduced through the arm 58 and through the first lumen 36 to fill the balloons 37 and 38 that any air within the balloon 38 will be urged out of the balloon through the vent tube 61 to the atmosphere. After the balloons 37 and 38 have been inflated in this manner and the air expelled therefrom, the radiographic contract liquid can be removed to deflate the balloons 37 and 38 so that they can be introduced into the vessel of the patient.

It should be appreciated that different means can be utilized for venting the distal balloon of the dual balloon catheter than the use of the vent tube hereinbefore described. For example, self venting means of the type described in applications Ser. Nos. 760,637 filed July 30, 1985, now U.S. Pat. No. 4,638,805, and 000,651, filed Jan. 6, 1987 can be utilized.

The apparatus 11 also includes a guide wire 66 of a conventional type, as for example, an 0.018 Hi-Torque Floppy (trademark) Guide Wire manufactured and sold by Advanced Cardiovascular Systems, Inc. of Mountain View, Calif. The guide wire 66 has proximal and distal extremities 67 and 68. In utilizing the guide wire, the proximal extremity of the same is inserted into the distal extremity of the balloon dilatation catheter 13 by introducing the same into the second lumen 46 and pushing it along the second lumen 46 until it exits through the inlet opening 47. After passing through the inlet opening, it is passed along the entire length of the tubular member 31 until the proximal extremity extends to or beyond the adapter 56.

The apparatus 11 also includes a removable slit sheath 71 formed of a suitable material such as high density polyolefin. The sheath 71 as shown in FIG. 2 can have suitable dimensions, as for example, an outside diameter of 0.050 inches and an inside diameter of 0.040 inches. It is provided with a slit 72 extending longitudinally of the same. The sheath 71 can have any suitable length but is preferably should extend up to and in close proximity to the proximal extremity of the first balloon 37. Thus, by way of example, with a balloon dilatation catheter having a length as, for example, 135 centimeters, the sheath would have a length of approximately 110 centimeters with the distance from the proximal extremity of the first balloon 37 and the distal extremity of the second balloon of approximately 20 centimeters. As shown the sheath 71 can be placed over the shaft of the balloon dilatation catheter 13. In this position, it can be seen that it locates or positions the guide wire 66 adjacent the shaft of the balloon dilatation catheter formed by the tubular member 31. In addition, the sheath 71 supplements and aids in the pushability of the balloon dilatation catheter.

Another embodiment of a balloon dilatation catheter incorporating the present invention is shown in FIG. 5 and is one in which the guide wire is enclosed along its entire length rather than a portion of the same being placed in a split sheath as shown in FIG. 1. This balloon dilatation catheter 76 consists of a flexible elongate tubular member 77 formed of a suitable plastic such as a polyolefin and has varying stiffness to increase pushability of the catheter. This is accomplished in the manner hereinbefore described utilizing different mixtures of high density and low density polyolefins. The tubular member 77 is provided with proximal and distal extremities 78 and 79. The tubular member 77 is provided with a first lumen 81 which extends from the proximal extremity of the tubular member to a region adjacent the distal extremity 79. This first lumen 81 can have a suitable diameter, such as approximately 0.012 inches in the region of FIG. 6 and a dimension of approximately 0.024×0.011 inches in the region of FIG. 7. First and second or proximal and distal inflatable balloons 82 and 83 of the type hereinbefore described are also carried by the tubular member 77 and are secured thereto in the manner hereinbefore described. The interior 84 of the first balloon 82 is placed in communication with the first lumen 81 by an elongate shot 81 extending between the first lumen 86 and the interior 84. The interior 87 of the second balloon 83 is also in communication with the distal extremity of the first lumen 81 through an elongate slot 88.

A second lumen 91 is carried by the tubular member 77 and extends from the proximal extremity to the distal extremity of the tubular member 77. This second lumen 91 should have a suitable size which is large enough to accommodate a guide wire and thus can have an inside diameter, as for example, approximately 0.021 inches in the region of FIG. 6 and a size of approximately 0.041×0.029 inches in the region of FIG. 7. The tubular member 77 in the region of FIG. 6 can have an outside diameter of approximately 0.044 inches and in the region of FIG. 7 have an outside diameter of approximately 0.060 inches. As can be seen, this second lumen 91 extends through the first and second balloons 82 and 83. An opening 92 is provided in the tubular member 77 just proximal of the proximal extremity of the first balloon 82 and is in communcation with the second lumen 91. Alternatively, a plurality of such openings 92 can be provided in communication with the second lumen 91. Alternatively, a plurality of such openings 92 can be provided in communication with the lumen 98 such as by providing a plurality of spaced apart notches extending over approximately five centimeters or greater as shown in FIG. 8 just proximal of the balloon 82.

The distal extremity of the tubular member 77 is provided with a plurality of longitundinally and circumferentially spaced holes 93 distal of the distal or second balloon 83 which are in communication with the flow passage or second lumen 91 to permit blood perfusion as hereinafter described. A radiopaque marker 94 of the type hereinbefore described is provided on the tubular member 77 within the distal balloon 83. Also a radiopaque marker 95 is placed on the member 77 just distal of the balloon 82.

An adapter 96 is mounted on the proximal extremity of the tubular member 76 and is comprised of a central arm 97 which is in communication with the second lumen 91. A guide wire 98 of conventional construction as, for example, the 0.018 Hi-Torque Floppy guide wire manufactured and sold by Advanced Cardiovascular Systems, Inc., of Mountain View, Calif. can be utilized. This guide wire 98 can be inserted in a conventional manner. It is provided with proximal and distal extremities 99 and 101. Thus by way of example, the distal extremity 101 can be inserted through the central arm 97 and the guide wire threaded through the second lumen 91 until the distal extremity 101 extends beyond the distal extremity of the tubular member 77. Alternatively, if desired, the proximal extremity 99 can be threaded through the distal extremity of the tubular member 77 and pushed rearwardly through the second lumen 91 until it extends out of the central arm 97 of the adapter 96 as shown in FIG. 5.

The adapter 96 is also provided with side arms 102 and 103. Suitable means is provided for venting the distal or second balloon 83 and as shown consists of a vent tube 106 of a conventional type as, for example, a flexible stainless steel tube which is introduced through the side arm 102 and extends through the first lumen 81 into the interior of the second balloon 83. The other side arm 103 can be utilized for introducing radiopaque contract liquid by use of a suitable device such as disclosed in U.S. Pat. No. 4,439,185. As the radiopaque contrast liquid is introduced into the side arm 103, the balloons 82 and 83 are inflated. Any air entrapped within the balloon 83 will be forced out to the atmosphere through the vent tube 106. After it has been observed that the balloon 83 has been filled with a radiopaque contrast liquid without any air bubbles therein, the balloon can be deflated by withdrawing the radiopaque liquid so that the balloon dilatation catheter is ready for use.

Operation and use of the apparatus 11 comprising the guiding catheter 12 and the balloon dilatation catheter 13 or alternatively, the balloon dilatation catheter 76 in performing the method of the present invention may now be briefly described as follows. Let it be assumed that it is desired to perform an angioplasty procedure in which it is believed that blood perfusion will be necessary because of the length of time that it is desired to inflate the dilatation balloon in the stenosis. The guiding catheter 12 is inserted into a vessel of the patient in a conventional manner by the use of a separate guide wire. Let it be assumed that it is desired to utilize balloon dilatation catheter 76. The catheter 76 after it has been prepared is inserted through the adapter 21 of the guiding catheter 12 by opening of the knob 23 and then closing it down around the catheter to minimize the loss of blood. The dilatation catheter is advanced in a conventional manner first by advancing the guide wire 98 and then advancing the catheter 76 over the guide wire 98 to the desired position. Let it be assumed that the guide wire 98 has been advanced into the stenosis and that the distal or second balloon 83 has been advanced into the stenosis and that it is now desired to inflate the same for a relatively lengthy period of time. Since this is the case, it is desirable to perfuse blood through the dilatation catheter. This can be readily accomplished by removing the guide wire and then taking blood from a suitable location as, for example, the femoral artery of the patient and pumping the same by use of a conventional pump and supplying the blood to the arm 24 of the guiding catheter 12. The arm 24 is in communication with the flow passage 18 of the guiding catheter 12 and flows through this relatively large passage up to the point of the first balloon 82 which occludes the flow passage and prevents the flow of blood in the flow passage 18 beyond that point. The blood then must pass through at least one the opening 92 into the second lumen 91 and then through the openings 93 distal of the second balloon 83. Blood therefore flows through the dilatation catheter into a region beyond the stenosis so that there is a continued supply of blood to the heart muscle during the period of inflation of the balloon. Thus, relatively long balloon inflation periods can be utilized if desired without any possibility of damage to the heart muscle.

By utilizing such apparatus, it has been found that normal proximal coronary arterial flow of approximately 60 cubic centimeters per minute can be readily achieved at relatively low pressures with minimum turbulence and hemolysis. By way of example, pressures near 25 psi can be utilized to achieve such flow rates utilizing the construction of the present invention. After the stenosis has been dilated for a sufficient period of time, the balloons 82 and 83 can be deflated and the balloon dilatation catheter 13 removed. Thereafter, the guiding catheter 12 can be removed.

It should be appreciated that the balloon dilatation catheter 13 can be also utilized in the guiding catheter 12 to perform the procedure hereinbefore described. Before introduction of the catheter 13 into the guiding catheter 12, the removable slit sheath 71 is placed over the tubular member 31 proximal of the first balloon 37 so that the guide wire 66 is retained therein. With this sheath 71 in place, the catheter 13 can be introduced into the guiding catheter 12 with the guide wire 68 preceding the distal extremity of the dilatation catheter 13. The sheath introducer 71, in addition to locating the guide wire 66 as hereinbefore described also facilitates the introduction of the catheter 13 into the guiding catheter 12 by increasing the stiffness of the shaft of the catheter 13.

After the catheter 13 has been positioned in the desired location, the proximal extremity of the sheath 71 can be grasped and it can be slipped off of the catheter 13 by peeling it away from the catheter through the slit 72.

After the distal or second balloon 38 has been positioned in the lesion, the guide wire 66 can be removed so that the flow passage 46 is free for the passage of blood to be perfused. The operation of this balloon dilatation catheter 13 and the guiding catheter 12 thereafter is substantially identical to that hereinbefore described for the balloon dilatation catheter 76. After the procedure for inflating the stenosis has been completed, the balloon dilatation catheter 13 and the guiding catheter 12 can be removed in the manner hereinbefore described.

With the apparatus hereinbefore described it can be seen that the distal balloon can be utilized as a standard dilatation balloon while the proximal balloon remains within the guiding catheter and during inflation is used to seal the distal end of the guiding catheter which permits blood to be pumped into the proximal end of the guiding catheter via the side arm 24 of the rotating hemostatic valve 22. Blood pumped down the guiding catheter uses the large inside diameter of the flow passage 18. This provides a low resistance to the flow of blood and thereby reduces pressures over the first 110 centimeters of the catheter system. Blood enters the dilatation catheter in a region adjacent the proximal extremity of the proximal balloon through an enlarged opening or multiple openings and continues through the relatively large guide wire/flow lumen or second lumen provided in the dilatation catheter. Blood travels beyond the second balloon and perfuses through the plurality of openings provided in the distal extremity of the catheter.

It also should be appreciated that in conjunction with the present invention, specific diameters and sizes have been given for the various components that different sizes and diameters can be utilized as desired to provide smaller and larger dilatation catheters.

Another alternative embodiment is to provide a large proximal balloon extending over substantially the entire 110 centimeters of the dilatation catheter connecting the distal extremity of the same into the guide wire/flow lumen and limiting the relatively short length proximal balloon. In utilizing such an embodiment, when blood is pumped into the catheter, it would be pumped in to fill the long 110 centimeter balloon which would expand and seal the dilatation catheter within the guiding catheter. This would still make it possible to take advantage of the large inside diameter of the guiding catheter to provide a large flow passage for the flow of blood through substantially the entire length of the dilatation catheter.

What is claimed is:

1. In a perfusion-type balloon dilatation apparatus, a guiding catheter having proximal and distal extremities and having a fluid flow passage extending therethrough, a balloon dilatation catheter disposed in the guiding catheter, the balloon dilatation catheter comprising a flexible elongate tubular member having proximal and distal extremities and having inflation means extending therethrough, first and second inflatable balloons carried by the tubular member and having their interiors in communication with the inflation means in the tubular member, the first balloon being positioned within the guiding catheter, the second balloon being positioned adjacent the distal extremity of the tubular member, a fluid flow lumen carried by the tubular member extending through the first and second balloons and through the distal extremity of the tubular member, the fluid flow lumen having an opening proximal of the first balloon and opening into the interior of the guiding catheter and an adapter carried by the proximal extremity of the guiding catheter and providing a liquid-tight seal between the guiding catheter and the dilatation catheter and also providing an inlet through which liquid can be introduced so that it can travel through the flow passage in the guiding catheter and the fluid flow lumen in the dilatation catheter so that the liquid can flow through the fluid flow lumen beyond the second inflatable balloon.

2. Apparatus as in claim 1 together with a guide wire extending through the fluid flow lumen having proximal and distal extremities, the distal extremity of the guide wire being adapted to extend beyond the distal extremity of the flexible elongate tubular member of the dilatation catheter, the proximal extremity of the guide wire being adapted to extend beyond the proximal extremity of the flexible elongate member of the dilatation catheter.

3. Apparatus as in claim 2 wherein the guide wire extends out of the opening for the fluid flow lumen proximal of the first balloon and extends rearwardly along the length of the flexible elongate tubular member of the dilatation catheter to a region beyond the proximal extremity of the dilatation catheter.

4. Apparatus as in claim 3 together with a slit sheath closing the flexible elongate tubular member in the region of the proximal extremity thereof and also enclosing at least a portion of the guide wire extending from the opening in the fluid flow lumen through the proximal extremity of the same.

5. Apparatus as in claim 2 wherein the fluid flow lumen extends to the proximal extremity of the flexible elongate tubular member and wherein the guide wire extends through the fluid flow lumen to the proximal extremity thereof.

6. Apparatus as in claim 1 wherein said first balloon is of relatively short length and is disposed near the distal extremity of the guiding catheter.

7. Apparatus as in claim 6 wherein the first balloon has a size sufficient so that when it is inflated it occludes the flow passage in the guiding catheter.

8. In a balloon dilatation catheter for use in a guiding catheter of the type having a flow passage extending therethrough, the balloon dilatation catheter comprising a flexible elongate tubular member having proximal and distal extremities, inflation means extending therethrough, first and second inflatable balloons the interiors of which are in fluid communication with the inflation means in the tubular member, the first balloon being positioned in a longitudinally spaced-apart position from the second balloon so that it is adapted to be positioned within a guiding catheter when the balloon dilatation catheter is disposed in the guiding catheter, the first balloon having a size so that when it is inflated, it will occlude the flow passage in the guiding catheter, the second balloon being disposed adjacent the distal extremity of the flexible tubular member, and a fluid flow lumen carried by the tubular member and extending through the first and second balloons and through the distal extremity of the tubular member, the fluid flow lumen having an opening proximal of the first balloon distal of the proximal extremity of the tubular member, and an adapter carried by the proximal extremity of the tubular member having an arm in fluid communication with the inflation means.

9. A catheter as in claim 8 wherein said fluid flow lumen extends the entire length of the flexible elongate tubular member.

10. A dilatation catheter comprising a flexible elongate tubular member having proximal and distal extremities, first and second longitudinally spaced apart inflatable ballons, inflation and deflation means in fluid communication with the interiors of the balloon, a fluid flow lumen within the tubular member extending through the first and second balloons and through the distal extremity of the tubular member, the fluid flow lumen having an opening proximal of the first balloon and a guide wire which extends through the fluid flow lumen out of said opening proximal of the first balloon and along the flexible elongate tubular member exteriorally thereof to a region which is beyond the proximal extremity of the flexible elongate tubular member.

11. Apparatus as in claim 10 together with a removable split sheath mounted on the proximal extremity of said elongate tubular member and enclosing the same and said guide wire.

12. In a method for perfusing blood beyond a stenosis in a vessel of a patient while accomplishing an angioplasty procedure, introducing a guiding catheter into the vessel of the patient, placing a guide wire into a dilatation catheter having a balloon on a distal portion thereof and inserting the guide wire and dilatation catheter into the guiding catheter while advancing the guide wire ahead of the dilatation catheter positioning the balloon of the dilatation catheter in the stenosis, occluding at least the distal extremity of the guiding catheter, providing a lumen in the dilatation catheter which extends from a position within the guiding catheter proximal of the portion which has been occluded through the distal extremity of the dilatation catheter and introducing blood into the lumen opening positioned within the guiding catheter and causing it to flow through the distal extremity of the dilatation catheter into the vessel of the patient beyond the stenosis and inflating the balloon to enlarge the opening in the stenosis.

13. In a method for performing an angioplasty procedure using perfusion, introducing a guiding catheter having a flow passage therein into the vessel of the patient, introducing a dilatation catheter with a fluid flow lumen extending longitudinally therein having longitudinally spaced apart first and second balloons carried thereby into the guiding catheter so that the distal balloon is positioned in the stenosis and the proximal balloon is positioned within the guiding catheter, inflating the proximal balloon to occlude the flow passage in the guiding catheter, inflating the distal balloon to dilate the stenosis, and introducing blood into the flow passage in the guiding catheter to cause the same to pass through the fluid flow lumen in the dilatation catheter to pass beyond and through the dilatation catheter beyond the stenosis to create a flow of blood in the vessel beyond the stenosis.

* * * * *

UNITED STATES PATENT AND TRADEMARK OFFICE
CERTIFICATE OF CORRECTION

PATENT NO. : 4,771,777

DATED : September 20, 1988

INVENTOR(S) : Michael J. Horzewski et al.

It is certified that error appears in the above-identified patent and that said Letters Patent is hereby corrected as shown below:

Column 1, line 37, delete "perfursion" and insert therefor --perfusion--.

Column 1, line 59, delete "guide" and insert therefor --guiding--.

Column 2, line 48, delete "provided" and insert therefor --provide--.

Column 3, line 7, delete "ballon" and insert therefor --balloon--.

Column 4, line 44, delete "contract" and insert therefor --contrast--.

Column 5, line 7, delete "is" and insert therefor --it--.

Column 5, line 67, delete "communcation" and insert therefor --communication--.

Column 5, line 68, bridging Column 6, line 1, delete the sentence "Alternatively, a plurality of such openings 92 can be provided in communication with the second lumen 91."

UNITED STATES PATENT AND TRADEMARK OFFICE
CERTIFICATE OF CORRECTION

PATENT NO. : 4,771,777
DATED : September 20, 1988
INVENTOR(S) : Michael J. Horzewski et al.

It is certified that error appears in the above-identified patent and that said Letters Patent is hereby corrected as shown below:

Column 6, line 8, delete "longitundinally" and insert therefor --longitudinally--.

Column 6, line 44, delete "contract" and insert therefor --contrast--.

Column 10, line 9, delete "ballons" and insert therefor --balloons--.1

Signed and Sealed this

Twentieth Day of March, 1990

Attest:

JEFFREY M. SAMUELS

Attesting Officer

Acting Commissioner of Patents and Trademarks